United States Patent
Borgert et al.

(10) Patent No.: US 9,820,672 B2
(45) Date of Patent: Nov. 21, 2017

(54) COLON SCREENING BY USING MAGNETIC PARTICLE IMAGING

(75) Inventors: Jörn Borgert, Hamburg (DE); Ingo Schmale, Hamburg (DE); Jürgen Erwin Rahmer, Hamburg (DE); Bernhard Gleich, Hamburg (DE); Michael Harald Kuhn, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 427 days.

(21) Appl. No.: 13/883,603

(22) PCT Filed: Nov. 7, 2011

(86) PCT No.: PCT/IB2011/054953
§ 371 (c)(1),
(2), (4) Date: May 6, 2013

(87) PCT Pub. No.: WO2012/063186
PCT Pub. Date: May 18, 2012

(65) Prior Publication Data
US 2013/0225979 A1    Aug. 29, 2013

(30) Foreign Application Priority Data
Nov. 11, 2010  (EP) .................................... 10190794

(51) Int. Cl.
*A61B 5/05*     (2006.01)
*A61K 49/18*    (2006.01)

(52) U.S. Cl.
CPC .............. *A61B 5/0515* (2013.01); *A61B 5/05* (2013.01); *A61K 49/1818* (2013.01)

(58) Field of Classification Search
CPC ...... A61B 5/05; A61B 5/0515; A61K 49/1818
See application file for complete search history.

(56) References Cited

U.S. PATENT DOCUMENTS

| 7,792,567 B2 | 9/2010 | Kuth |
| 2005/0266074 A1 | 12/2005 | Zilberstein et al. |
| 2006/0078790 A1 | 4/2006 | Kuth et al. |
| 2006/0241391 A1 | 10/2006 | Rabinovitz |
| 2007/0078335 A1* | 4/2007 | Horn ............................ 600/425 |
| 2008/0019917 A1 | 1/2008 | Pacey |
| 2008/0175459 A1* | 7/2008 | Geiger et al. ................ 382/131 |

(Continued)

FOREIGN PATENT DOCUMENTS

| WO | WO2006046155 | 5/2006 |
| WO | WO2006106507 | 10/2006 |

(Continued)

OTHER PUBLICATIONS

J. Weizenecker, et al., "Three-Dimensional Real-Time in Vivo Magnetic Particle Imaging", Physics of Medicine and Biology, 54 (2009) L1-L10.

(Continued)

*Primary Examiner* — Ruth S Smith

(57) ABSTRACT

A method for colon screening and collecting data by using Magnetic Particle Imaging wherein an imaging magnetic field is generated with a spatial distribution of the magnetic field strength such that the area of examination in the colon consists of a first sub-area with lower magnetic field strength, where the magnetization of a magnetic particle which was pre-delivered to the colon is not saturated, and a second sub-area with a higher magnetic field strength, where the magnetization of said magnetic particle is saturated. The spatial location of both sub-areas in the area of examination is modified so that the magnetization of said particles changes locally. Signals are acquired and are evaluated to obtain information about the spatial distribution of the signals in the area of examination. The method may be carried out during an entire peristaltic cycle in a colon portion or segment.

16 Claims, 4 Drawing Sheets

(56) References Cited

U.S. PATENT DOCUMENTS

| | | | |
|---|---|---|---|
| 2009/0069668 A1 | 3/2009 | Stemmer | |
| 2009/0092554 A1 | 4/2009 | Skaff et al. | |
| 2009/0148387 A1* | 6/2009 | Bikram | 424/9.322 |
| 2010/0149183 A1* | 6/2010 | Loewke et al. | 345/424 |
| 2010/0297026 A1* | 11/2010 | Doyle | 424/9.323 |
| 2013/0023714 A1* | 1/2013 | Johnston et al. | 600/1 |

FOREIGN PATENT DOCUMENTS

| | | |
|---|---|---|
| WO | WO2007034196 | 3/2007 |
| WO | WO2008078242 | 7/2008 |
| WO | WO2009067105 | 5/2009 |
| WO | WO 2009074952 A2 * | 6/2009 |

OTHER PUBLICATIONS

J. Borgert, et al., "Fundamentals and Applications of Magnetic Particle Imaging", Journal of Cardiovascular Computed Tomography (2012) 6, pp. 149-153.

B. Gleich, et al., "Fast MPI Demonstrator with Enlarged Field of View", Proc. Intl. Soc. Mag. Reson. Med. 18 (2010), pp. 218.

T. Lauenstein, et al., "MR Colonography Without Colonic Cleansing: A New Strategy to Improve Patient Acceptance", AJR: 177, Oct. 2001, pp. 823-827.

P.J. Pickhardt, et al., "Computed Tomographic Virtual Colonoscopy to Screen for Colorectal Neoplasia in Asymptomatic Adults", vol. 349, No. 23, Dec. 4, 2003, pp. 2191-2200.

F. Feng, et al., "Development of Oral Gastrointestinal Tract Contrast Agents for Magnetic Resonance Imaging", Chin. J. Med. ed. Imaging Technol. 2005, vol. 21, No. 7. pp. 1131-1132.

S. Chikazumi, "Langevin Theory of Paramagnetism", Physics of Ferromagnetism, John Wiley & Sons, Inc., New York, 1964, pp. 60-64.

Hayat, M.A., "Cancer Imaging vol. 2: Instrumentation and Applications", Academic Press, 2007.

Gleich, B. et al, "Tomographic imaging using the nonlinear response of magnetic particles", Nature, (2005), vol. 435, pp. 1214-1217.

Feng, F. et al., "Development of oral gastrointestinal tract contrast agents for magnetic resonance imaging", Chinese Journal of Medical Imaging Technology, 2005-2007.

* cited by examiner

COLON SCREENING BY USING MAGNETIC PARTICLE IMAGING

FIELD OF THE INVENTION

The present invention relates to a method for colon screening by using Magnetic Particle Imaging comprising the steps of: (a) generating an imaging magnetic field with a spatial distribution of the magnetic field strength such that the area of examination in the colon consists of a first sub-area of the colon with lower magnetic field strength, where the magnetization of a magnetic particle which was pre-delivered to the colon is not saturated, and a second sub-area of the colon with a higher magnetic field strength, where the magnetization of said magnetic particle is saturated; (b) changing the spatial location of both sub-areas in the area of examination so that the magnetization of said particles changes locally; (c) acquiring signals that depend on the magnetization in the area of examination influenced by this change; and (d) evaluating said signals to obtain information about the spatial distribution of the signals in the area of examination. The area of examination in the colon preferably comprises a portion or segment of the colon and steps (a) to (c) may be carried out during an entire peristaltic cycle in said colon portion or segment. The present invention further relates to a corresponding method for collecting data, the use of a magnetic particle for colon screening via Magnetic Particle Imaging, a food stuff or liquid for in vivo diagnostic use comprising a magnetic particle, and a method for preparing a patient for colon screening by using Magnetic Particle Imaging.

BACKGROUND OF THE INVENTION

Magnetic Particle Imaging (MPI) is a tomographic imaging technique, which relies on the nonlinearity of the magnetization curves of magnetic particles and the fact that the particle magnetization saturates at some magnetic field strength (Gleich et al., 2005, Nature, 435, 1214-1217). In a medical context MPI uses the magnetic properties of magnetic particles administered to the body to measure the particle concentration. Because a body contains no naturally occurring magnetic materials visible to MPI, there is no background signal. After intake, the MPI particles appear as bright signals in the images, from which particle concentrations can be calculated. By combining high spatial resolution with short image acquisition times, MPI can also capture dynamic concentration changes as the magnetic particles are moved. This allows MPI scanners to perform a wide range of functional measurements in a single scan.

Colon screening approaches are traditionally based on endoscopic colonoscopy, i.e. the examination of the colon and distal parts of the small bowel with a CCD camera or a fiber optic camera on a flexible tube passed through the anus. This technique allows for a visual diagnosis of the examined areas and grants the opportunity for biopsy and/or removal of lesions. However, endoscopic colonoscopy inter alia brings about a serious risk of gastrointestinal perforation which may be life threatening and requires immediate major surgery for repair.

An alternative, non-invasive technique is virtual colonoscopy or computed tomography (CT) colonography. CT colonography is a medical imaging method employing tomography created by computer processing. Digital geometry processing is used to generate a three-dimensional image of the inside of an object from a large series of two-dimensional X-ray images taken around an axis of rotation. During the procedure the patient is typically placed in a supine position on the examination table. Subsequently a thin tube is inserted into the rectum, so that air can be pumped through the tube in order to inflate the colon for better viewing. The table then moves through the scanner to produce a series of two-dimensional cross-sections along the length of the colon while the patient is asked to hold his/her breath to avoid distortion on the images. Although CT colonography bears only a strongly reduced risk of gastrointestinal perforation (mainly due to gas distension), the method bears a severe risk of radiation exposure. The radiation dose from a CT colonography is considered to be equivalent to several hundred chest x-rays. Accordingly, the risk of developing solid tumors from radiation due to CT colonography is assumed to be substantially higher than the risk of perforation from colonoscopy.

Moreover, endoscopic colonoscopy as well as CT colonography require a bowel-cleansing regimen which typically includes a low-fiber or clear-liquid only diet for one to three days, followed by the administration of laxatives and large quantities of fluids the days before the screening. This procedure leads to a severe discomfort of the patients and drastically decreases their compliance.

Document WO 2009/074952 discloses an arrangement and a method for influencing and/or detecting magnetic particles in a region of action. An objection of the application is the provision of an enhanced apparatus and a more effective method for combined hyperthermia treatment and magnetic particle imaging (MPI).

Document WO 2008/078242 discloses a similar arrangement and method for influencing and/or detecting magnetic particles in a region of action. An objection of the application is the improvement of the quality of the magnetic field generating means and/or the quality of the magnetic field detecting means.

Weizenecker et al., 2009, Phys. Med. Biol., 54 (L1-L10) discloses a three-dimensional real-time in vivo magnetic particle imaging. The document indicates a temporal resolution of 21.5 ms achieved at a 3D field of view of 20.4× 12×16.8 mm$^3$ with a spatial resolution sufficient to resolve all heart chambers.

US 2006/0241391 discloses a method and system for the detection of pathologies, e.g. the detection of cancer in the gastrointestinal tract utilizing MRI technology.

A further alternative to endoscopic colonoscopy and CT colonography is Magnetic Resonance (MR) colonography, which is based on the Magnetic Resonance Imaging (MRI) technique, i.e. the use of magnetic fields to align the magnetization of atoms of magnetic particles in the body, and the corresponding employment of radio frequency fields to systematically alter the alignment of this magnetization, which causes the nuclei to produce a rotating magnetic field detectable by a scanner. However, in MRI approaches the thresholds for in vitro and in vivo imaging are such that the background signal from the host tissue is a crucial limiting factor, thus limiting the resolution power of the method. Furthermore, MR colonoscopy still requires bowel cleansing or at least a distention of the colonic lumen involving the administration of contrast agents such as barium via rectal tubes (Lauenstein et al., 2001, American Journal of Roentgenology, 177, 823-827), which still entails a high level of unpleasantness for the patient.

There is thus a need for an alternative colonography method, which has an elevated patient acceptance while allowing colon screenings at a high resolution.

SUMMARY OF THE INVENTION

The present invention addresses this need and provides means and methods, which allow for colon screening by using the technique of Magnetic Particle Imaging. The above objective is in particular accomplished by a method for colon screening comprising the steps of:

(a) generating an imaging magnetic field with a spatial distribution of the magnetic field strength such that the area of examination in the colon consists of a first sub-area of the colon with lower magnetic field strength, where the magnetization of a magnetic particle which was pre-delivered to the colon is not saturated, and a second sub-area of the colon with a higher magnetic field strength, where the magnetization of said magnetic particle is saturated;

(b) changing the spatial location of both sub-areas in the area of examination so that the magnetization of said particles changes locally;

(c) acquiring signals that depend on the magnetization in the area of examination influenced by this change; and (d) evaluating said signals to obtain information about the spatial distribution of the signals in the area of examination.

This method provides several advantages: it is essentially non-invasive since apart from magnetic particles no medical device or instrument has to be introduced into the body. Furthermore, the higher temporal resolutional power of Magnetic Particle Imaging allows for the possibility of a segmental detection of signals along examined areas of the intestine and a compensation of peristaltic movements of the bowel. In consequence, the method does not require any bowel-cleansing regimen or distention of the colonic lumen, but entirely relies on the presence of magnetic particles in the bowel, which may be administered orally, e.g. together with food or liquids.

In a further aspect the present invention relates to a method for collecting data comprising the steps of:

(a) generating an imaging magnetic field with a spatial distribution of the magnetic field strength such that the area of examination in the colon consists of a first sub-area of the colon with lower magnetic field strength, where the magnetization of a magnetic particle which was pre-delivered to the colon is not saturated, and a second sub-area of the colon with a higher magnetic field strength, where the magnetization of said magnetic particle is saturated;

(b) changing the spatial location of both sub-areas in the area of examination so that the magnetization of said particles changes locally; and (c) acquiring signals that depend on the magnetization in the area of examination influenced by this change.

In a preferred embodiment of the present invention the step of changing the spatial location of the sub-areas comprises the generation of a spatially and temporarily varying magnetic field.

In a further preferred embodiment of the present invention the area of examination in the colon comprises a portion or segment of the colon.

In another preferred embodiment of the present invention steps (a) to (c) as mentioned above may be carried out during an entire peristaltic cycle in said colon portion or segment. Subsequently the area of examination may be reassigned to a different portion or segment of the colon. In a particularly preferred embodiment the area of examination may be reassigned to an adjacent portion or segment of the colon.

In another preferred embodiment of the present invention said method for colon screening as described above may comprise an evaluation step including a visualized reconstruction of all examined portions of the colon based on the acquired signals.

In a further preferred embodiment of the present invention the magnetic particle is to be pre-delivered to the colon. This pre-delivery may preferably be a pre-delivery via oral uptake, in particular with or within food stuff or a liquid.

In another aspect the present invention relates to the use of a magnetic particle for colon screening via Magnetic Particle Imaging.

In a preferred embodiment of the present invention said use for colon screening comprises examination of a portion or segment of the colon during an entire peristaltic cycle in said colon portion or segment, followed by a reassignment of the area of examination to a different portion or segment of the colon. In a particularly preferred embodiment of the present invention said reassignment of the area of examination is a reassignment of the area of examination to an adjacent portion or segment of the colon.

In another aspect the present invention relates to a food stuff or a liquid for in vivo diagnostic use comprising a magnetic particle.

In another aspect the present invention relates to a method for preparing a patient for colon screening by using Magnetic Particle Imaging, comprising the administration of a food stuff or liquid comprising a magnetic particle.

In a preferred embodiment of the present invention said colon screening or diagnostic use is a screening for cancerous diseases of the colon, colon inflammation, polyps, gastrointestinal patency or transit, or mucosa defects of the colon.

In a further preferred embodiment of the present invention said uptake or administration of food stuff or liquid is to be started 1 to 5 days before the screening.

In a particularly preferred embodiment of the present invention said magnetic particle is a coated and/or gastro resistant iron oxide particle. Alternatively, said magnetic particle may be or have a shell structure comprising an iron oxide particle. In a further particularly preferred embodiment said shell structure is a non-magnetic shell structure comprising iron oxide particles.

In a further particularly preferred embodiment of the present invention said coated iron oxide particle is polymer coated or latex coated. In yet another particularly preferred embodiment said shell structure comprises a polymer coated or latex coated iron oxide particle. Further preferred is a shell structure comprising a dispersion of polymer coated or latex coated iron oxide particles.

DETAILED DESCRIPTION OF EMBODIMENTS

Figure 1:
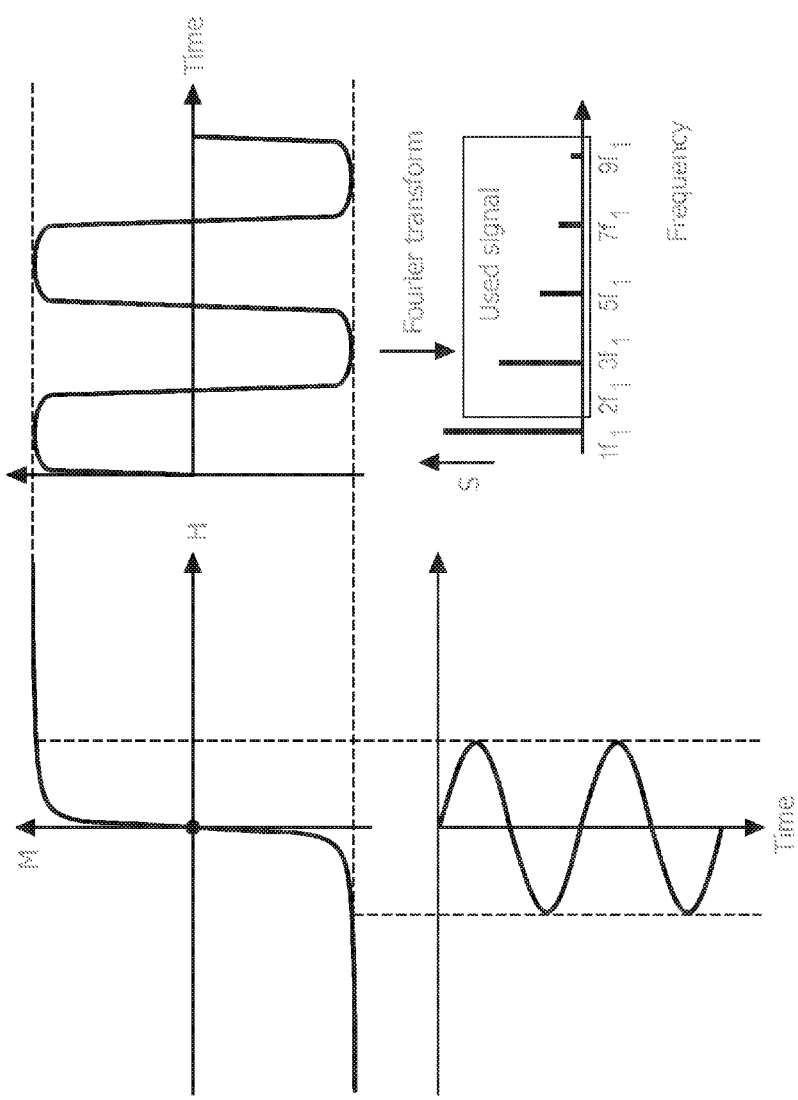
FIG. 1 shows the basic imaging principle of MPI. The send signal is composed of a time dependent, preferably sinusoidal homogeneous electromagnetic field. The magnetic particles reacts to the send signal with a change in magnetization. The change of magnetization can be described by Langevin theory (Chikazumi S, 1964, Physics of Magnetism; John-Wiley, New York) and can be detected as induced voltages in receive coils. As the change in magnetization is a non-linear phenomenon, the receive signal contains harmonies of the frequencies contained in the send signal. This case is present for regions of low field strength where the particles are not in saturation.
Figure 2:
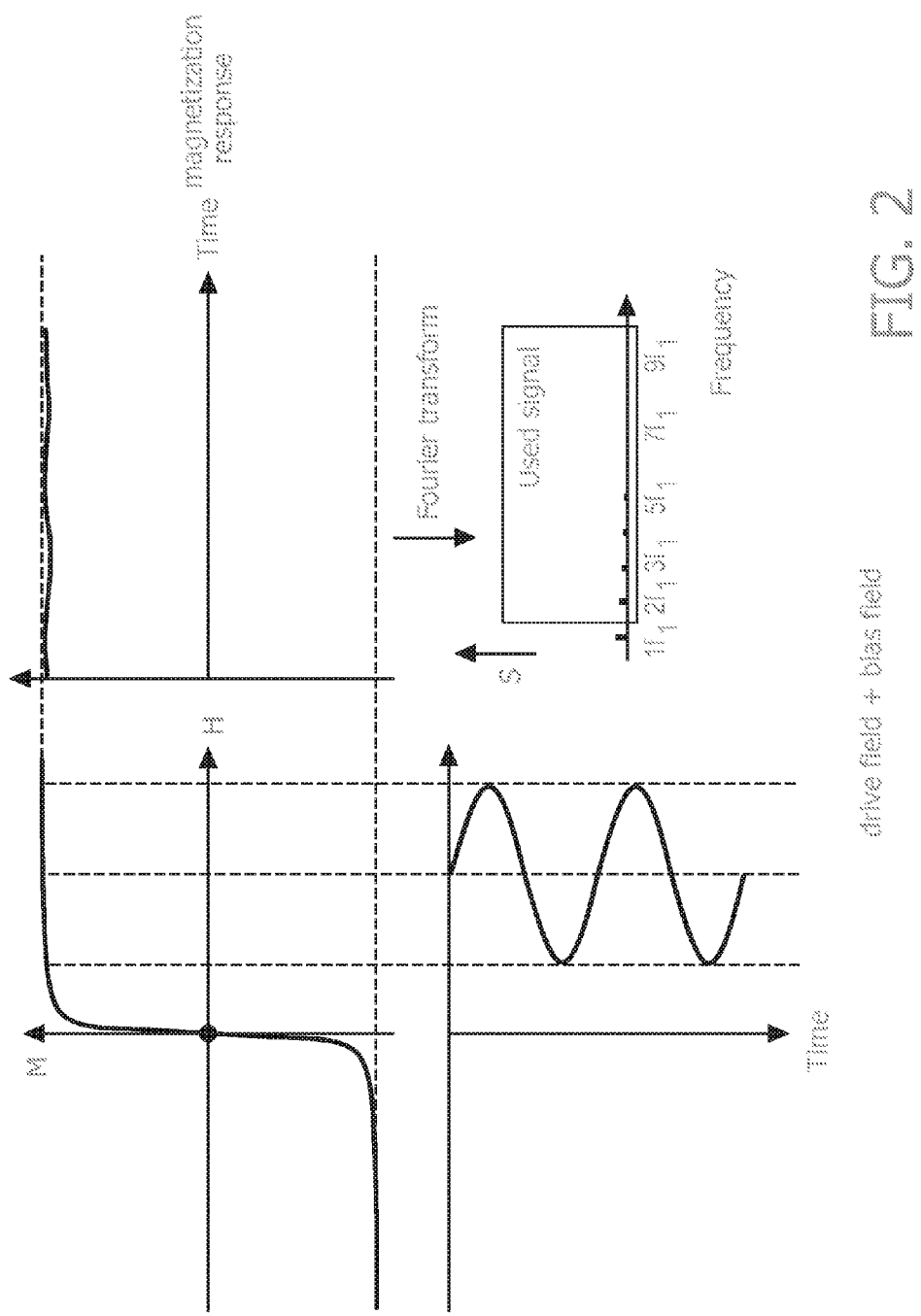
FIG. 2 depicts the case of higher field strength with particles already being in saturation. Any change in field strength due to the send signal results in only minor changes in magnetization. Hence, no harmonics can be detected and the resulting receive signal contains only the base frequencies of the send signal.
Figure 3:
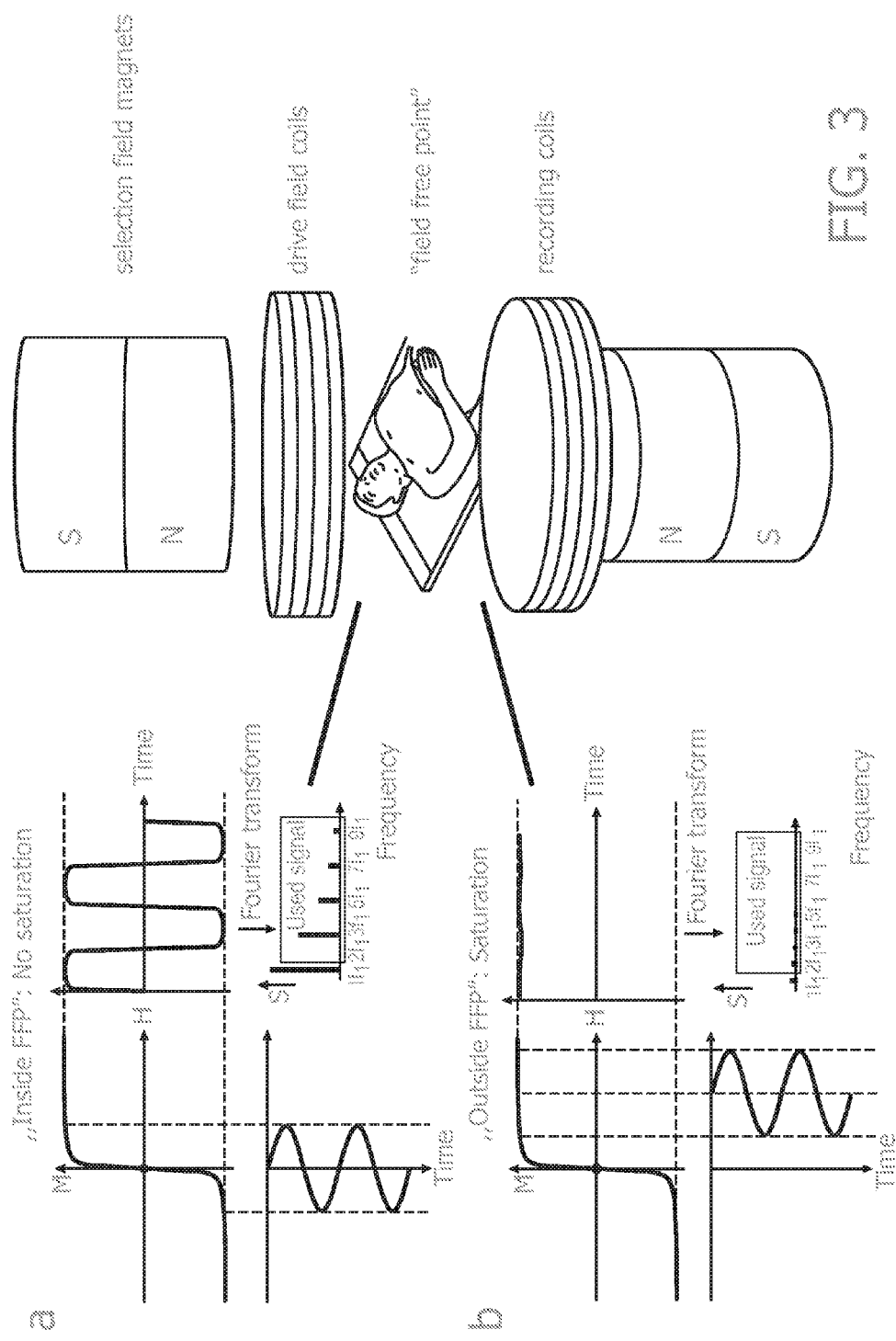
FIG. 3 shows a possible embodiment of a magnetic particle imaging scanner. Two magnets produce a field configuration with a region of low field strength (mathematically named the field free point) and regions of higher field strength. This field configuration can also be realized by coils in Maxwell configuration (opposing currents). When a send signal is present, the situation described in FIG. 1 is present at the area of low field strength and the situation of FIG. 2 is present in the other areas of higher field strength. This way, the determination of the concentration of the magnetic particles can be limited to the area of low field strength and it is possible to tell where the signal originates, realizing a 'spatial coding'. The patient is placed between the magnets and the concentration of magnetic particles can be determined. By moving the area of low field strength over the area of examination, the concentration of the magnetic particle can be determined for the area of interest of the patient, in this case, the colon.
Figure 4:
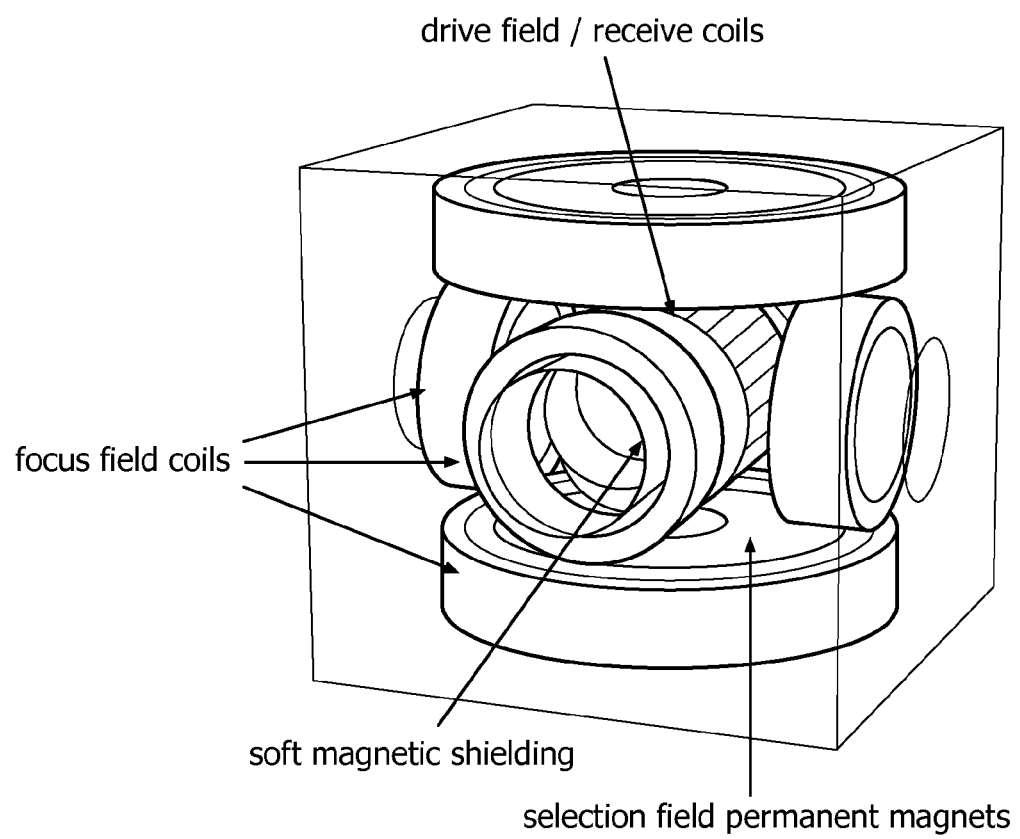
FIG. 4 Shows a MPI scanner set up including focus field coils.

The inventors have developed means and methods, which allow for colon screening by using the technique of Magnetic Particle Imaging.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a method for colon screening comprising the steps of:

(a) generating an imaging magnetic field with a spatial distribution of the magnetic field strength such that the area of examination in the colon consists of a first sub-area of the colon with lower magnetic field strength, where the magnetization of a magnetic particle which was pre-delivered to the colon is not saturated, and a second sub-area of the colon with a higher magnetic field strength, where the magnetization of said magnetic particle is saturated;

(b) changing the spatial location of both sub-areas in the area of examination so that the magnetization of said particles changes locally;

(c) acquiring signals that depend on the magnetization in the area of examination influenced by this change; and (d) evaluating said signals to obtain information about the spatial distribution of the signals in the area of examination.

The term "colon screening" as used herein refers to an examination of the colon and/or adjacent parts of the human or animal body. The term "colon and/or adjacent parts" as used herein refers colon and parts of the gastrointestinal tract in its vicinity. In certain embodiments, the screening may be carried out for the entire gastrointestinal tract or other parts thereof outside of the colon, including, for example, such parts as the stomach, the small intestine, the duodenum, the jejunum, the ileum, the cecum, the appendix or sub-divisions thereof. The area of examination may also comprise any combination of parts of the gastrointestinal tract as mentioned above. Preferred is an examination of the colon.

The term "screening" as used herein refers to an analytical or visual examination via a reproduction of the structures, elements and/or modifications of said structures or elements in the examined areas, as well as a comparison of the obtained information with control or standard values, images, or information. The screening preferably aims at the identification of anomalous structures, elements, regions, and/or pathological situations and/or their changing over time. Examples of such anomalous structures, elements, regions, and/or pathological situations are growths in the examination area, deviant functional conditions etc. The examination may preferably be carried out in vivo. Alternatively, pathological examinations are also envisaged by the present invention. The examination is preferably non-invasive or essentially non-invasive. In specific embodiments one or more invasive steps may be included.

In step (a) a spatially inhomogeneous magnetic field may be generated. In a typical embodiment the magnetic field strength in a first sub-area of the area to be examined may be so weak that the magnetization of a magnetic particle differs more or less significantly from an external magnetic field. The magnetization may accordingly be not saturated. The first sub-area may have different forms or shapes, be continuous or discontinuous. Preferably, it is a spatially continuous area, e.g. a spot- or dot-like area, a line or an area of a typical geometrical form, e.g. a rectangle, trapezoid, cuboid, circle, tube, triangle etc. In a further typical embodiment the magnetic field strength in a second sub-area, which is preferably the area of examination outside of the first sub-area, the magnetic field strength may be sufficiently high in order to keep the magnetic particles in state a of saturated magnetization.

The term "saturated" as used herein refers to a state in which the magnetization of almost all particles is oriented essentially in the direction of the outer magnetic field. In such a state an increase of the magnetic field strength may preferably not contribute to any significant increase of magnetization in comparison to the magnetization in the first sub-area.

Suitable magnetic particles to be used in the method are those that can reach saturation with a sufficiently small magnetic field. Typically, the magnetic particles have a minimum size or a minimum dipole moment in order to achieve this criterion. The term "magnetic particle" as used herein thus means particles that can be magnetized. Suitable magnetic particles may preferably have dimensions that are small compared to the size of the voxel whose magnetization is to be determined by the method according to the invention. In addition, the magnetization of the particles should preferably reach saturation at the lowest possible field strengths of the magnetic field.

The lower the field strength required for this is, the higher the spatial resolution capacity or the weaker the (external) magnetic field being generated in the area of examination can be. In addition, the magnetic particles may preferably have the highest possible dipole moment or a high saturation induction so that the change in magnetization produces the largest possible output signals. The magnetic particle should in a particularly preferred embodiment not to be toxic.

The magnetic particle in said area of examination may be present, i.e. pre-delivered, in the area in a concentration sufficiently high to allow the above characterized process.

The term "area of examination" refers in a preferred embodiment to the colon and/or adjacent parts. In addition or in the alternative, other parts of the gastrointestinal tract may also be an area of examination. Examples of such parts are the stomach, the small intestine, the duodenum, the jejunum, the ileum, the cecum, the appendix or sub-divisions thereof. The area of examination may also comprise the entire gastrointestinal tract or any combination of parts of the gastrointestinal tract as mentioned above.

The term "pre-delivered" means that the magnetic particles have been provided, localized or allocated to the area of examination, in particular the colon, but additionally or alternatively also to further areas of the gastrointestinal tract, e.g. the stomach, the small intestine, the duodenum, the jejunum, the ileum, or the large intestine, the cecum, the appendix or sub-divisions thereof etc. via any suitable means. For example, a magnetic particle may have been provided, localized or allocated to said gastrointestinal regions via oral uptake, enemas, or direct placements, e.g. via surgical intervention. The pre-delivered particles may be present in a homogenous concentration, i.e. essentially equal concentrations, over the gastrointestinal tract, preferably over the colon, more preferably over the area of examination of the colon. Alternatively, the pre-delivered magnetic particles may be present in non-homogenous concentrations over the gastrointestinal tract, preferably over the colon, more preferably over the area of examination of the colon. The pre-delivered magnetic particles may, for example show concentration gradients in different directions, e.g. in the axial direction of the gastrointestinal tract, in particular of the colon, i.e. in the direction of the tubular structures, or in a radial direction, e.g. from the center to the outer parts of the tubular structure. Furthermore, the pre-delivered magnetic particles may show local variations of concentration due to internal structure of the gastrointestinal tract, e.g. protrusions, folding, wrinkles etc, or due to content of the gastrointestinal tract, e.g. the content of water or liquids, the food or type of food ingested. Preferred is a high concentration homogeneity.

In step (b) the spatial location of both sub-areas in the area of examination as defined above may be changed. This variation may preferably lead to a state in which the magnetization of the pre-delivered magnetic particles changes locally. In particular, by varying the spatial location of both sub-areas in the area of examination the overall magnetization in the area of examination may be changed. In some embodiments, the spatial location of both sub-areas in the area of examination may be varied by a movement of magnets or magnetic coils used for the generation of the magnetic field relative to the patient or the area of examination, or by a movement of the patient or area of examination relative to said magnets or magnetic coils Accordingly, the magnetization in the area of examination and/or physical parameters directly associated with said magnetization may be measured, i.e. signals may be acquired which depend on the magnetization in the area of examination influenced by the change of spatial location of the sub-areas (step (c)). Preferably, signals may be obtained by changing the spatial position of both sub-areas as rapidly as possible. A coil, with which a magnetic field can be generated in the area of examination, can be used to acquire the signals. Preferably, at least one separate coil is used.

These data, i.e. signals characterizing the magnetization in the area, may subsequently be used to derive information about the spatial distribution of the pre-delivered magnetic particles in the area of examination, e.g. the colon or adjacent structures. These signals may accordingly be collected, mathematically transformed according to suitable algorithms, optionally subjected to a statistical evaluation, and finally visualized in one or more images of the area of examination. Implementations and details would be known to person skilled in the art, e.g. from qualified textbooks, in particular publications relating to MPI or CT methods, e.g. "Bildgebende Systeme für die medizinische Diagnostik"; Heinz Morneburg (Hrsg.), 3. Auflage, Publicis MCD Verlag, Erlangen, 1995; or "Digitale Bildverarbeitung", Bernd Jähne, 5. Ausgabe, Springer Verlag, Berlin, Heidelberg, New York, 2002.

In a further aspect the present invention relates to a method for collecting data comprising the steps of:

(a) generating an imaging magnetic field with a spatial distribution of the magnetic field strength such that the area of examination in the colon consists of a first sub-area of the colon with lower magnetic field strength, where the magnetization of a magnetic particle which was pre-delivered to the colon is not saturated, and a second sub-area of the colon with a higher magnetic field strength, where the magnetization of said magnetic particle is saturated;

(b) changing the spatial location of both sub-areas in the area of examination so that the magnetization of said particles changes locally; and (c) acquiring signals that depend on the magnetization in the area of examination influenced by this change.

Steps (a) to (c) correspond to steps (a) to (c) as defined herein above in the context of the method for colon screening. Data such as signals mentioned in step (c) may be acquired according to any suitable method known to the person skilled in the art. The data may be directly saved on suitable media or be deposited in an ordered manner, e.g. in a suitable database. In a specific embodiment of the present invention the method for collecting data as mentioned above may be a method for collecting data on anomalous structures, elements, regions, and/or pathological situations and/or their changing over time of the colon or adjacent parts, and/or other portions of the gastrointestinal tract. In a further embodiment, the method of data acquisition may be combined with a method of data analysis, e.g. a method employing a visualization algorithm, and/or a statistical analysis method determining the quality or usability of the data. Furthermore, the method of data acquisition may be combined with a subsequent method of data transformation, data visualization and/or data comparison.

In a preferred embodiment of the method for colon screening or the method for collecting data the step of changing the spatial location of the sub-areas may comprise the generation of a spatially and temporarily varying magnetic field. Thus, in order to change the spatial position of both sub-areas in the area of examination or to change the magnetic field strength in the first sub-area, an e.g. magnetic field that is localized and/or changes over time may be generated. If the change in the spatial position of the sub-area is implemented by using a magnetic field changing over time, this can induce a similarly periodic signal in a coil.

In a certain embodiments of the present invention potential difficulties in the acquisition of the signal due to the simultaneous effectivity of the signals generated in the area of examination and the magnetic field changing over time may be avoided in that a magnetic field changing over time acts on a first frequency band on the area of examination and that a second frequency band, which may contain higher frequency components than the first frequency band, in the signal received from the coil is evaluated to obtain information about the spatial distribution of the magnetic particles. This exploits the fact that the frequency components of the second frequency band can only be created by a change in the magnetization in the area of examination due to the non-linearity of the magnetization characteristic curve. When the magnetic field changing over time has a sinusoidal periodic behavior, the first frequency band may consist only of a single frequency component, i.e. the sinusoidal fundamental oscillation. In contrast, the second frequency band may contain, in addition to this fundamental oscillation, higher harmonics, e.g. harmonic waves, of the sinusoidal fundamental oscillation, which may preferably be used for evaluation.

A preferred arrangement for the method for colon screening or the method for collecting data in the present invention is characterized in that the means for generating the magnetic field includes a gradient coil arrangement for generating a magnetic gradient field, which reverses its direction in the first sub-area of the area of examination and evidences a zero passage. This magnetic field is—when the gradient coil arrangement, e.g. comprises two identical windings carrying opposing flows located on either side of the area of examination (Maxwell coil)—zero at a point on the winding axis and increases almost linearly on both sides of this point with opposite polarities. It is only with these particles located in the area around this field zero point where magnetization is not saturated. For particles outside this area, the magnetization is in a state of saturation. Therefore an arrangement can be provided with means to generate a magnetic field changing over time and superimposed on the magnetic gradient field for the purpose of moving both sub-areas in the area of examination. The area generated by the gradient coil arrangement may therefore be moved around the field zero point, i.e. the first sub-area, within the area of examination by the magnetic field changing over time. With appropriate changes over time and orientation of this magnetic field it may accordingly be possible to move the field zero point throughout the entire area of examination.

The magnetization change resulting from the movement of the field zero point may be detected by an appropriate coil arrangement. The coil used to detect the signals generated in the area of examination can be a coil that is already used to generate the magnetic field in the area of examination. In a further embodiment a separate coil may be used for the reception as this can be decoupled from the coil arrangement producing a magnetic field that changes over time. In addition, an improved signal/noise ratio can be achieved with a coil and more so with several coils.

The amplitude of the signals induced in the coil arrangement increases the faster the position of the field zero point changes in the area of examination, i.e. the faster the magnetic field changing over time superimposed on the magnetic gradient field changes. Particularly preferred arrangements comprise means to generate a first and at least a second magnetic field superimposed on the magnetic gradient field, where the first magnetic field moves slowly with high amplitude and the second magnetic field moves fast with low amplitude. This generates—preferably by two coil arrangements—two magnetic fields with different speeds and different amplitudes.

In a further embodiment of the method for colon screening or the method for collecting data the field changes can be very fast (e.g. >20 kHz) such that they lie above the human limit of audibility. In a further embodiment both magnetic fields in the area of examination may be generally aligned vertically to one another. This may enable the movement of the field free point within a two-dimensional area. This may further can be expanded to a three-dimensional area by another magnetic field comprising a component aligned vertically to the two magnetic fields.

In yet another embodiment an arrangement with a filter downstream of a coil arrangement is envisaged, which suppresses the signal components in a first frequency band in the signal induced by the coil arrangement and allows the signal components in a second frequency band, which contains higher frequency components than the first frequency components, to pass. The magnetization characteristic curve may accordingly be non-linear in the area where the magnetization changes from the non-saturated to the saturated state. As a consequence a sinusoidal magnetic field over time may generate in the area of non-linearity an induction changing over time.

In a further embodiment of the method for colon screening or the method for collecting data of the present invention the magnetic particles may become saturated when an external magnetic field is applied with a strength of about 100 mT/$\mu$0 or less. Larger saturation field strengths are also suitable for the method according to the invention.

Further suitable magnetic field strengths are about 10 mT/$\mu$0 or less. It is also possible to achieve good measurement results with field strengths in the area of 1 mT/$\mu$0 or less, or about 0.1 mT/$\mu$0 or less. For example, concentration data, temperature, pressure or pH values can be determined with high accuracy and resolution with magnetic fields of circa 10 mT/$\mu$0 or less, about 1 mT/$\mu$0 or less or about 0.1 mT/$\mu$0 or less.

In a further embodiment the magnetic field strengths may be adapted to specific individual parameters of the patient or the part of the gastrointestinal tract to be examined, e.g. the patient's size, weight, age, sex, the size of the area to be examined, its physiological condition, the amount or concentration of magnetic particles administered or present in the area of examination etc. These parameters may be determined and the corresponding values can be set by the skilled person according to known data or information from the corresponding technical field. Such a process may be carried out before the examination or dynamically during the examination or during or between steps or cycles of the examination. In a further embodiment, also the employment of fixed or non-changed parameters are envisaged.

In further embodiments of the method for colon screening or the method for collecting data of the present invention the field strength of the varying magnetic field may be at least two times, preferably three times higher than the field strength of the imaging magnetic field. The field strength of the varying magnetic field may essentially be made dependent on the size and nature of the magnetic particles. Suitable calculation schemes would be known to the person skilled in the art, or can be derived from qualified textbooks or publications, e.g. Chikazumi S, 1964, Physics of Magnetism; John-Wiley, New York.

In a particularly preferred embodiment the field strength and the frequency of the varying magnetic field should be set to a value high enough to prevent clumping or agglomeration of magnetic particles, and at the same time to a value sufficiently low to prevent damage the object of examination or lesions in the examined patient. Furthermore, the field strength and the frequency of the varying magnetic field should be set to a value, which prevents that the varying magnetic field heats up the organism and/or the examined tissue or tissue regions. In the preferred embodiment the varying magnetic field should accordingly have a power input of less than 500 Watt, more preferably of less than 300 W. These values are average values over about 10 seconds. Thus, actual peak values may be higher. In a particularly preferred embodiment, the field strength of the varying magnetic field may be less than 10 mT/µ0.

In further embodiments the varying magnetic field may be applied in intermittent pulses such that the average power input is less than 300 to 500 W. For example, when a continuous wave with 20 mT/µ0 at 100 kHz is applied, a patient would still be below the heat limit. Higher amplitudes than that may be applied, but then it may only applied in short bursts.

In a further embodiment of the present invention the frequency of the varying magnetic field may be at any suitable value, e.g. between about 0.5 and 1.5 MHz, preferably between about 0.7 and 1.3 MHz.

In a further embodiment the frequency of the varying magnetic field and/or the energy input may be adapted to specific individual parameters of the patient or the part of the gastrointestinal tract to be examined, e.g. the patient's size, weight, age, sex, the size of the area to be examined, its physiological condition, the amount or concentration of magnetic particles administered or present in the area of examination etc. These parameters may be determined and the corresponding values can be set by the skilled person according to known data or information from the corresponding technical field. Such a process may be carried out before the examination or dynamically during the examination or during or between steps or cycles of the examination. In a further embodiment, also the employment of fixed or non-changed parameters are envisaged.

In another preferred embodiment of the method for colon screening or the method for collecting data of the present invention the area of examination in the colon comprises a portion or segment of the colon. The term "portion or segment of the colon" as used herein refers to a sector or fragment of the entire colon. Preferred is a sector or fragment of the colon which can be analysed with a suitably high resolution allowing a detailed visualization of the area or the collection of corresponding data. The exact size of the portion or segment of the colon to be examined may depend on the type, size or coating of the magnetic particle used, the concentration of the magnetic particle in said sector, the magnetic field used, the field strength of the varying magnetic field, the power input, the size and/or physiology of the patient to be examined, the peristaltic movements of the patient and/or further parameters. The area of examination may accordingly be set to a specific value in accordance with these parameter or other suitable parameters as known to the person skilled in the art. The size of the area of examination may in a further embodiment be changed or varied during the examination, e.g. in a zoom in or zoom out manner, or it may be kept fix. An example of a preferred area of examination of a portion or segment of the colon is an area of about 10 cm×10 cm. Further envisaged are areas having a smaller or bigger size, e.g. a size of about 5 cm×5 cm, 15 cm×15 cm, 20 cm×20 cm, 10 cm×5 cm, 10 cm×15 cm, 15 cm×5 cm, 20 cm×10 cm, 20 cm×5 cm, 20 cm×15 cm or any other suitable size.

In a further alternative embodiment of the present invention, the area of examination may also be a portion or segment of other parts of the gastrointestinal tract. For example, the area of examination may comprise a sector or fragment of the stomach, the small intestine, the duodenum, the jejunum, the ileum, the cecum, the appendix or subdivisions or transition regions between these sectors or between these sectors and the colon, where applicable. Accordingly, a preferred area of examination of a portion or segment of the gastrointestinal tract or its subdivisions is an area of about 10 cm×10 cm. Further envisaged are areas of the gastrointestinal tract or its subdivisions having a smaller or bigger size, e.g. a size of about 5 cm×5 cm, 15 cm×15 cm, 20 cm×20 cm, 10 cm×5 cm, 10 cm×15 cm, 15 cm×5 cm, 20 cm×10 cm, 20 cm×5 cm, 20 cm×15 cm or any other suitable size.

In a further embodiment, areas of examination may overlap, e.g. overlap with each other. The overlap may be an overlap of between about less than 1% to about 90% or more. Preferred is an overlap of about 20-50% between adjacent areas. Alternatively, there may be no overlap between the areas of examination.

In yet another embodiment of the present invention, the area of examination or selection field of the colon or gastrointestinal tract may be adapted to specific individual parameters of the patient or parameters of the part of the gastrointestinal tract to be examined, e.g. the patient's size, weight, age, sex, the size of the area to be examined, its physiological condition, the amount or concentration of magnetic particles administered or present in the area of examination etc. These parameters may be determined and the corresponding values can be set by the skilled person according to known data or information from the corresponding technical field. Such a process may be carried out before the examination or dynamically during the examination or during or between steps or cycles of the examination. In a further embodiment, also the employment of fixed or non-changed parameters are envisaged.

In another preferred embodiment of the present invention the steps of generating an imaging magnetic field with a spatial distribution of the magnetic field strength (a), changing the spatial location of both sub-areas in the area of examination (b) and acquiring signals that depend on the magnetization in the area of examination influenced by this change (c) of the method for colon screening or the method for collecting data as defined herein above may be carried out during an entire peristaltic cycle in the colon portion or segment.

The term "entire peristaltic cycle" as used herein refers to one peristaltic wave which forces a ball or bolus of ingested material, e.g. food, along the gastrointestinal tract, in particular along the colon. The wave or peristaltic movement may be initiated by circular smooth muscles contracting behind the ball or bolus of ingested material to prevent receding of the material, and is typically followed by a contraction of longitudinal smooth muscles pushing the material forward. In a preferred embodiment, the peristaltic cycle may thus comprise the contracting of both muscle groups. In further, alternative embodiments, the method may also be carried out during a part of the entire peristaltic cycle, e.g. only during the contraction of one of the mentioned muscle groups, e.g. the circular smooth muscles or the longitudinal smooth muscles.

In further preferred embodiments, the method may be repeated during more than one peristaltic cycle, e.g. once, twice, three times, four times, 5 times, 6 times, 7 times, 8 times or more often be repeated, i.e. the same area of examination may be examined once, twice, three times, four times, 5 times, 6 times, 7 times, 8 times or more often during 1, 2, 3, 4, 5, 6, 7, 8, or more peristaltic cycles. The cycles may be subsequent cycles or timely discontinuous cycles, e.g. every second, third, fourth cycle etc.

The period of the peristaltic cycle further depends on the area of examination. By varying said area of examination the period of the peristaltic cycle may accordingly be varied.

It is, thus, an advantage of the present invention that the examination may be carried out during peristaltic movements of the colon or gastrointestinal tract. Due to the relatively small size of the area of examination as well as the physical properties of the Magnetic Particle Imaging technique the methods of the invention thus allow a colon screening without the necessity of influencing the normal peristaltic movements of a patient.

In specific embodiments, in particular in case of very fast peristaltic movements, or in case a patient shows spasms, or in order to enhance qualitatively critical images the peristaltic movement may be influenced by the administration of suitable medicaments to a patient to be examined. For example, a parasympatholyticum, e.g. butylscopolaminbromide or derivates therefrom may be used. Further suitable medicaments would be known to the person skilled in the art.

Furthermore, in particular in case of patient movements or an increased nervousness of the patient, or in order to enhance qualitatively critical images a suitable tranquilizer or calmative agent may be administered to the patient to be examined, e.g. a benzodiazepine, preferably lorazepam or diazepam. Further examples of suitable tranquilizers would be known the person skilled in the art.

In a further particularly preferred embodiment of the present invention the performance the steps of generating an imaging magnetic field with a spatial distribution of the magnetic field strength (a), changing the spatial location of both sub-areas in the area of examination (b) and acquiring signals that depend on the magnetization in the area of examination influenced by this change (c) of the method for colon screening or the method for collecting data as defined herein above during an entire peristaltic cycle in a specific colon portion or segment, i.e. a specific area of examination as defined above, is followed by a reassignment of said area of examination to a different portion or segment of the colon or gastrointestinal tract. The "different" portion or segment of the colon or gastrointestinal tract may be any other segment of the colon or gastrointestinal tract or any specific area of examination of another segment of the colon or gastrointestinal tract. Such further specific areas may be located in the vicinity of the previously examined areas, or may be dislocated. It is preferred that the different or next portion or segment of the colon or gastrointestinal tract to be examined is an adjacent portion or segment of the colon or gastrointestinal tract. "Adjacent" as used herein means that the portion may either have a common border with the previously examined area or section, or be at least partially overlapping therewith. The overlap may be an overlap of between about less than 1% to about 90% or more. Preferred is an overlap of about 10% to about 50%, e.g. an overlap of 10%, 15%, 20%, 25%, 30%, 35%, 40% or 45%.

The area of examination may accordingly be reassigned to the next or adjacent portion or segment of the colon or gastrointestinal tract to be examined. Such a reassignment may be carried out by moving the patient within an MPI apparatus, or by moving the apparatus or coils necessary for the generation of the magnetic field and its detection.

In a particularly preferred embodiment of the present invention an additional electromagnetic field, i.e. a focus field, may be used for the colon screening method as described herein above.

More preferably, the reassignment of the area of examination may be improved by the employment of a focus field or the implementation of the focus field technique for MPI.

The term "focus field" as used in the context of the present invention relates to a homogenous, temporarily variable electromagnetic field. This field may be present in addition to a magnetic field described herein above, i.e. a drive field or receive field. Preferably, the focus field may be based on an additional set of coils (focus field coils) which are able to provide up to about 500 mT/μ0. These coils may further exhibit a much lower frequency than drive field coils. In a typical embodiment, a focus field may have a magnetic field strength of up to about 500 mT/μ0, e.g. about 100 mT/μ0, 110 mT/μ0, 120 mT/μ0, 130 mT/μ0, 140 mT/μ0, 150 mT/μ0, 160 mT/μ0, 170 mT/μ0, 180 mT/μ0, 190 mT/μ0 or 200 mT/μ0, 210 mT/μ0, 220 mT/μ0, 230 mT/μ0, 240 mT/μ0, 250 mT/μ0, 260 mT/μ0, 270 mT/μ0, 280 mT/μ0, 290 mT/μ0, 300 mT/μ0, 310 mT/μ0, 320 mT/μ0, 330 mT/μ0, 340 mT/μ0, 350 mT/μ0, 360 mT/μ0, 370 mT/μ0, 380 mT/μ0, 390 mT/μ0, 400 mT/μ0, 410 mT/μ0, 420 mT/μ0, 430 mT/μ0, 440 mT/μ0, 450 mT/μ0, 460 mT/μ0, 470 mT/μ0, 480 mT/μ0, 490 mT/μ0 or 500 mT/μ0 and a frequency of up to 100 Hz, e.g. of about 50 Hz, 60 Hz, 70 Hz, 80 Hz, 90 Hz, 95 Hz or 100 Hz. The focus field may accordingly shift the area, which is scanned by the drive field to cover a certain volume, for example a volume of 10×10×10 cm$^3$. To maintain fast acquisition, the focus field typically has to shift the rapidly encoded area by the linear dimensions of the patch within its encoding time. For example, for an encoding time of more than 10 ms, the focus field strength for one shift may be about 40 mT/μ0, resulting in a slew rate of less than 4 T/μ0/s, which allows field changes well below the field changes due to the gradient coils in a clinical MRI scanner.

In a specific embodiment of the present invention soft magnetic material may be introduced into MPI scanner in order to guide the focus field flux. The soft magnetic material may preferably be used in the housing of a field generator cube. In addition, the stray field may be shielded. In a further preferred embodiment the soft magnetic material may be shielded by aluminum plates in order to avoid the generation of harmonics that could interfere with the detection of the magnetic particles' signals. The thickness of the plates may be adapted to suitable values as known to the person skilled in the art in order to prevent the drive field from penetrating the shielding, but to allow for transparency with respect to the low frequency focus field.

Additional features and details would be known to the person skilled in the art and can be derived from Gleich et al., "Fast MPI Demonstrator with Enlarged Field of View, 2010", International Society for Magnetic Resonance in Medicine Meeting, May 1-7 2010, Abstract 218.

In a further particularly preferred embodiment of the method for colon screening as described herein above the evaluation of signals to obtain information about the spatial distribution of the signal in the area of examination comprises a reconstruction of the examined portions of the colon based on the acquired signals. In one embodiment, such reconstruction may be carried out with suitable algorithms and/or computer programs or devices known to the skilled person. Preferred is the employment of algorithms and/or computer programs or devices developed for the reconstruction and visualization of CT data or signals. Suitable algorithms and further features and details would be known to the person skilled in the art, and/or may be derived from qualified publications, e.g. Pickhardt et al., 2003, N Engl J Med, 349, 2191-2200.

The reconstruction may in a specific embodiment be carried out by selecting data for one or more overlapping sections of the examined portion or segment of the colon or of the entire region examined and a subsequent combination of these data including a correction step for redundant data or information.

In a further embodiment, the reconstruction may include the use of a second or further dataset obtained from a patient, e.g. a dataset obtained from a repetition of the examination during two or peristaltic cycles in an area of examination.

In yet another embodiment, the reconstruction may further or additionally be based on previously obtained data from the same patient, or be based on data obtainable from a database or information repository.

Reconstructed sections of the colon or of other portions of the gastrointestinal tract according to the present invention may be visualized according to any suitable method, e.g. as 2D or 3D visualizations, based on suitable computer graphic systems or medical graphic systems or diagnostic devices.

In a particularly preferred embodiment of the present invention, the method for colon screening as described herein above provides a visualized reconstruction of the examined portions of the colon or the gastrointestinal tract of a patient, in which the resolution is high enough in order to visualize structures of size of about 10 mm, preferably of a size of about 6 to 10 mm, more preferably of a size of about 1 to 6 mm, even more preferably structures of around 0.85 to 1.5 mm, e.g. structures of a size or diameter of, 0.85 mm, 0.9 mm, 1.0 mm, 1.1 mm, 1.2 mm, 1.5 mm. The method for colon screening as described herein above may further provide a visualized reconstruction of the examined portions of the colon or the gastrointestinal tract of a patient, which shows the entire colon or at least all examined sections, e.g. also including regions which are blocked or otherwise inaccessible by endoscopic methods.

In yet another embodiment the method of data collection as described herein above may be combined with a step of visual reconstruction as defined herein above.

In another preferred embodiment of the method for colon screening or the method for collecting data the mentioned magnetic particle is to be pre-delivered to the colon or gastrointestinal tract via an oral uptake of a food stuff or liquid. Typically, a food stuff or liquid which comprises a magnetic particle has been ingested by the patient one or more days before the examination.

In a preferred embodiment, said uptake may take place for a period of time of about 1 to 5 days, e.g. 1 day before the examination, 2 days before the examination, 3 days before the examination, 4 days before the examination, or 5 days before the examination or longer. The length of the administration period may be adjusted by the concentration of magnetic particles to be taken orally, i.e. in the food stuff or liquid, and/or the patient's physiology, size, age, weight, sex etc.

A food stuff or liquid in the context of the present invention may be any suitable food stuff or liquid known to the person skilled in the art, preferably food suited for forming non-clumped stool or homogenous stool. For example, the food stuff may comprise a portion of dietary fiber, e.g. between about 5% and 50% of dietary fiber. The food stuff should in a further embodiment not comprise a high degree of protein or fat. A liquid may preferably comprise components, which cover or bind the magnetic particles. In particular, the food stuff or liquid should not contain or comprise components which enhance the excretion of the magnetic particles, in particle of iron oxide particles.

The food stuff or liquid to be taken orally in order to achieve a pre-delivery of magnetic particles in the colon or gastrointestinal tract may comprise said magnetic particle in any suitable concentration. The concentration may be set to a value as high as possible without negatively influencing the flavor of the food stuff or liquid, and/or without becoming toxic to the patient or providing other negative effects to the patient.

The oral uptake may be an uptake together with ordinary meal, or may be an uptake between ordinary meals, e.g. in mid-morning, mid-afternoon or after dinner. The uptake may take place every 1 hour, 2 hours, 3 hours, 4 hours, 5 hours, 6 hours, 8 hours, 10 hours, 12 hours, 24 hours, 48 hours or at any other suitable period of time. The uptake may be adjusted according to physiological conditions of the patient, its daily rhythm etc.

In a further specific embodiment the method for colon screening or the method for collecting data as described herein above comprises as additional first step or step (0) the step of administering to a patient to be examined a magnetic particle. Preferably said administering may be an administering of a food stuff or liquid comprising said magnetic particle. In these embodiments the magnetic particles are not pre-delivered, but are administered during the first step of the methods.

In another aspect the present invention relates to the use of a magnetic particle for colon screening via Magnetic Particle Imaging. Thus, a magnetic particle, in particular a magnetic particle as mentioned herein, may be used for an examination of the colon or gastrointestinal tract according to the established principles of Magnetic Particle Imaging known to the person skilled in the art, or derivable form qualified textbooks or publications such as Gleich and Weizenecker, 2005, Tomographic imaging using the nonlinear response of magnetic particles, Nature, 435, 1214-1217; or Weizenecker et al., 2009, Three-dimensional real-time in vivo magnetic particle imaging, Phys. Med. Biol., 54:L1-L10.

Preferred is the use of a magnetic particle for an examination of the colon or gastrointestinal tract as defined herein above. Further preferred is the use of a magnetic particle for colon screening following at least one of the steps (a) to (d) of the method for colon screening as defined herein above.

Thus, in a preferred embodiment of the present invention, the use of a magnetic particle for colon screening via Magnetic Particle Imaging comprises the use of said particle for the examination of a portion or segment of the colon or gastrointestinal tract.

In a more specific embodiment, the use of said particle for the examination of a portion or segment of the colon or gastrointestinal tract comprises the examination during an entire peristaltic cycle in said colon portion or segment or portion or segment of the gastrointestinal tract, as described herein above.

In yet another more specific embodiment, the use of said particle for the examination of a portion or segment of the colon or portion or segment of the gastrointestinal tract during an entire peristaltic cycle in said colon portion or segment comprises a reassignment of the area of examination to a different portion or segment of the colon or gastrointestinal tract, as described herein above.

In yet another particularly preferred embodiment, the use of said particle for the examination of a portion or segment of the colon during an entire peristaltic cycle in said colon portion or segment or portion or segment of the gastrointestinal tract followed by a reassignment of the area of examination to a different portion or segment of the colon or gastrointestinal tract comprises a reassignment to an adjacent portion or segment of the colon or gastrointestinal tract.

In another aspect the present invention relates to a food stuff or liquid for in vivo diagnostic use comprising a magnetic particle. A food stuff for in vivo diagnostic use according to the present invention may be a foodproduct or edible provided with or enriched with a magnetic particle, in particular a magnetic particle as described herein. Preferably, the food is suited for forming non-clumped stool or homogenous stool. Examples of such foodstuff are bread, soup, yoghurt, cereals, potato based meals, convenience foods comprising different ingredients, meat, or sweets such as chocolate, jellies etc. Other types or classes of food stuff are also envisaged. The food stuff may comprise a proportion of about 0.001 to about 6% w/w of magnetic particles.

A liquid for in vivo diagnostic use according to the present invention may be a beverage or drink, provided with or enriched with a magnetic particle, in particular a magnetic particle as described herein. Preferably the liquid is suited for forming non-clumped stool or homogenous stool. Examples of such liquids are water, milk, fruit juice, tea, coffee, soft drinks, vegetable juice, beer or wine. Other types or classes of liquids are also envisaged. Preferred are non-alcoholic beverages, in particular juices and soft drinks. The liquids may comprise a proportion of about 0.001 to about 6% w/w of magnetic particles.

In a particularly preferred embodiment, the food stuff or liquid is freed from components which enhance the excretion of the magnetic particles, in particle of iron oxide particles, or the amount of these components is significantly reduced.

The present invention further envisages a production method for such food stuff or liquid as well as the use of a magnetic particle for the production of a food stuff or liquid for in vivo diagnostic use.

In another aspect the present invention relates to a method for preparing a patient for colon screening by using Magnetic Particle Imaging, comprising the administration of a food stuff or liquid comprising a magnetic particle. The term "preparing a patient" as used herein refers to the setting of physiological and medical conditions of a patient that is scheduled to undergo a colon screening by Magnetic Particle Imaging as described herein. Preferably, the term relates to the provision and enrichment of magnetic particles suitable for Magnetic Particle Imaging in the patient's region of examination. The patient's preparation particularly comprises in one embodiment the administration of food stuff or liquids according to the present invention, i.e. food stuff or liquids comprising a magnetic particle as defined herein.

In a preferred embodiment said method for preparing a patient for colon screening comprises the administration of a food stuff or liquid in a time window of about 1 to 5 days before the screening, i.e. examination. The administration may, for example, be started 5 days before the screening, 4.5 days before the screening, 4 days before the screening, 3.5 days before the screening, 3 days before the screening, 2.5 days before the screening, 2 days before the screening, 1.5 days before the screening, 1 day before the screening, or half a day before the screening. Furthermore, the administration may be started at any point in time between the indicated points. Furthermore, the administration may be started earlier. In further embodiments the administration scheme may be adjusted to the patient's physiology, size, sex, weight, its typical meal size, the concentration of magnetic particles present in the food stuff or liquid or any other suitable parameter known to the person skilled in the art.

In a further embodiment of the present invention, the method of preparation may be accompanied by a control step or control method, in which the amount of excreted magnetic particle is measured. In accordance with results from said control step and/or the calculated concentration of magnetic particles in the colon or gastrointestinal tract, the type of food stuff or liquid and/or the concentration of magnetic particles in said food stuff or liquid may be adjusted or varied.

In an alternative embodiment, the method for preparing a patient for colon screening by using Magnetic Particle Imaging may additionally comprise a step of bowel cleansing, e.g. several days in advance of the screening in order to be able to provide a specifically defined composition of ingredients in a patient's gastrointestinal tract, or in case a patient is afflicted by constipation. In a further alternative embodiment the method for preparing a patient for colon screening by using Magnetic Particle Imaging may additionally comprise a step of colon distension. In yet another alternative embodiment the method for preparing a patient for colon screening by using Magnetic Particle Imaging may additionally comprise the administration of a parasympatholyticum in order to reduce peristaltic movements, e.g. butylscopolaminbromide or derivates therefrom. This step may preferably be carried out immediately before the screening starts.

In a further preferred embodiment of the present invention, the colon screening or diagnostic use as mentioned herein above is a screening for cancerous diseases of the colon, colon inflammation, polyps, gastrointestinal patency or transit, or mucosa defects of the colon. The term "cancerous disease of the colon" as used herein refers to any typical cancer or tumor of the colon, e.g. colorectal cancer, adenocarcinoma, a squamous cell carcinoma or a lymphoma of the colon. In a further embodiment, also cancerous diseases of other portions of the gastrointestinal tract may screened or identified in the context of the present invention. This group of cancerous diseases comprises cancer of the rectum, cancer of the appendix, small intestine cancer, duodenal cancer, intestinal neoplasms, gastrointestinal stromal tumor, ileal carcinoid tumor or gastric carcinoma. In a particularly preferred embodiment of the present invention the colon screening is a screening for anomalous growth forms, structures, elements, regions, and/or pathological situations and/or their changing over time. An example of such growth forms is a polyp, i.e. an abnormal growth of tissue projecting from the mucous membrane of the colon or other parts of the gastrointestinal tract. More preferably, the present invention envisages a screening for polyps of an abnormal, increased size, e.g. a size of more than 3, 4, 5, or 6 mm, more preferably of a size of more than 6 mm, e.g. 8, 9, or 10 mm.

In further specific embodiments the screening of the colon or the gastrointestinal tract may be a screening for inflammatory modifications of the examined areas, e.g. colon inflammations, gastric inflammations, small intestine inflammation etc.

In a further embodiment of the present invention the colon screening may be a screening in regions of constipation, in which endoscopic approaches are not possible or are connected with a high risk of lesions.

In yet another specific embodiment of the present invention, the colon screening or screening of the gastrointestinal tract may be a gatekeeper process or first step of a two or three partite diagnostic approach and/or be combined with a subsequent CT colonography or preferably an endoscopic colonoscopy. For example, in case the colon screening or screening of the gastrointestinal tract according to the present invention results in the identification of one or more potentially problematic situations, in particular the presence of one or more polyps of a suspicious size or form, the screening may be complemented in a further step by an endoscopic colonoscopy. Preferably, the colonoscopy may be restricted to sections, which have been preselected in the colon screening according to the present invention. Such an approach provides the advantage that only in those cases in which the non-invasive colon screening according to the present invention has shown abnormal modifications in the examined areas an invasive and less pleasant endoscopic screening has to be carried out.

In a further embodiment of the present invention the magnetic particle to be employed for the present invention may be a particle that can be reverse magnetized by Neel rotation and/or that the reverse magnetization is caused by Brownian rotation.

A magnetic particle according to the present invention may be composed of any suitable material known to the person skilled in the art. For example, the particle may be composed of magnetic material, preferably of Fe, Co, Ni, Zn, Mn etc. or chemical derivatives thereof. Typical derivatives which are also envisaged by the present invention are alloys or oxides of metals, e.g. alloys or oxides of Fe, Co, Ni, Zn or Mn or any combination thereof. Also encompassed by the present invention are magnetic particles composed of ferrite material or of doped materials, e.g. Co, Ni, Zn or Mn:$Fe_xO_y$. Particularly preferred are oxides of iron, e.g. $Fe_2O_3$ or $Fe_3O_4$ and/or non-stoichiometric magnetic iron oxides.

In some embodiments the size of a magnetic particle according to the present invention may vary between a diameter of about 5 nm and 50 nm. Preferably, the size of a magnetic particle is about 15, 20, 25, 30 or 35 nm. More preferably, the diameter is >15 nm, even more preferred is a diameter of about 30 nm.

In a particularly preferred embodiment of the present invention the magnetic particle to be employed for the present invention is a coated magnetic particle, more preferably a coated iron oxide particle. A coat or coating according to the present invention may be a suitable envelop for a single particle, which ensures that particles do not agglomerate or are damaged or modified. Such coats or coatings may, for example be polymeric, e.g. based on the presence of carbohydrate molecules, or the presence of glycosylation pattern, or the presence of PEG (polyethylene glycol). In a further preferred embodiment the coat or coating should ensure a safe passage of the particle through the stomach into the intestine, in particular into the colon. Particularly preferred in this respect are latex coated particles, particles coated with silicates, or gastroresistant particles. An example of a coating which may be suitable within the context of the present invention is the coating of the AMI-121 (Lumirem or Gastromark) particle, or the coating of the OMP (Abdoscan) particle, which may be used for the coating of a magnetic particle as described herein. Further examples of such coatings as well as additional details or features thereof would be known to the person skilled in the art and/or can be derived from qualified publications such as M. A. Hayat, "Cancer imaging: Instrumentation and applications", Vol. 2, Academic Press, $1^{st}$ ed, 2007.

In another preferred embodiment of the present invention a magnetic particle is also to be understood as a shell structure or container comprising one or more magnetic particles, preferably a multitude of magnetic particles, in particular a shell structure comprising one or more iron oxide particles, preferably a multitude of iron oxide particles. The term "shell structure" as used herein refers to an envelope like structure, which is typically comprised of small units or entities, which have identical or similar chemical, physical and/or biological properties. Furthermore, the envelope-like structure forms a cavity, i.e. excludes the exterior environment from the interior and hence serves as a boundary between exterior and interior environments, conditions etc. Shell structures according to the present invention may preferably be composed of a hydrophobic layer. The layer may be a monolayer or a bilayer. The sides of a bilayer structure may have different properties and/or be composed of different shell-forming units. Preferably, both sides will comprise hydrophobic tail structures pointing towards the interior of the shell structure or membrane. The shell structure may for example have a multilamellar form or a unilamellar form, constituting, for example, a small or large multilamellar vesicle, a small unilamellar vesicle or a large unilamellar vesicle. The shell structure may have any suitable form or dimension, e.g. the shell structure may be spherical, it may be elliptical, it may be circular or pear-shaped, dumb-bell like, flattened, pyramidal, sphere-like, e.g. as rigid sphere etc. The shell structure may further be capable of self-assembly.

In a typical embodiment of the present invention, the shell forming units may be comprised of hydrophobic tails and hydrophilic heads. The interior or cavity of the shell structure may preferably constitute a hydrophilic environment, e.g. an aqueous solution. Alternatively, the cavity of the shell structure may be comprised of a hydrophilic environment. The environment of the cavity of the shell structure may comprise the same environmental conditions as the exterior, or different environmental conditions. The term "environmental condition" as used herein refers to pH, the concentration of organic or inorganic ions, the presence of one or more salts, the presence of osmotic pressure etc. For instance, the pH in the cavity of the shell structure may be lower, identical or higher than the pH at the exterior, there can be osmotic pressure in the shell structure or there may be osmotic equilibrium etc.

In addition to shell-forming units, the shell may comprise further elements, which provide additional functions.

Examples of such additional elements are targeting entities, which allow an interaction and/or recognition of the shell structure by compatible elements, or stabilizing or destabilizing elements, which modify the chemical, physical and/or biological properties of the shell structure. These elements are typically present at the outside or outer surface of the shell structure and may or may not protrude into the interior of the shell structure and/or the cavity of the shell structure. Particularly preferred are elements, which allow a targeting of the shell structure to specific tissue types, specific organs, cells or cell types or specific parts of the body, in particular the animal or human body, more preferably to parts or portions of the gastrointestinal tract, e.g. the colon, or to tissue types present in said body parts, e.g. mucosal regions. For example, the presence of targeting entities may lead to a targeting of the shell structures to such tissues or organ parts, in particular in the gastrointestinal tract or colon. Alternatively, the presence of targeting entities may lead to a targeting to specific cell types, e.g. cancerous cells or polyps, which express an interacting or recognizable protein at the surface. In a preferred embodiment of the present invention the shell structure may comprise proteins or peptides or fragments thereof, which offer an interaction surface at the outside and/or inside of the shell structure. Examples of such protein or peptide elements are ligands which are capable of binding to receptor molecules, receptor molecules, which are capable of interacting with ligands or other receptors, antibodies or antibody fragments or derivatives thereof, which are capable of interacting with their antigens, lectins etc.

The shell structure may also be covered by additional compounds, preferably by compounds which increase its stability and/or circulatory life, influence its biodistribution, modify its immunological behavior etc.

In a further preferred embodiment of the present invention the shell structure may be composed of or be covered by gastroresistant components, or be suitable for a safe passage through the stomach and/or the intestine and/or the colon.

A particularly preferred shell structure may be coated with or externally be composed of silicates or derivatives thereof or functional analogues thereof.

In a further preferred embodiment a shell structure as described herein above itself may be non-magnetic.

In a further preferred embodiment, such a non-magnetic shell structure may comprise, essentially comprise or contain a group of single magnetic particles, more preferably a group of single iron oxide particles as described herein.

In a further preferred embodiment, such a shell structure may comprise, essentially comprise or contain a group of coated iron oxide particles, more preferably of polymer coated iron oxide particles, latex coated iron oxide particles or a mixture thereof. In yet another preferred embodiment of the present invention such a non-magnetic shell structure may comprise, essentially comprise or contain a dispersion of magnetic particles, more preferably of iron oxide particles as described herein, which may help to avoid an agglomeration of the particles. The amount of comprised particles may vary in dependence of the particle nature, the type of shell structure used, the presence of further ingredients etc.

Typically, between about $1 \times 10^6$ to $1 \times 10^8$ particles may be present in a shell structure according to the present invention or in a dispersion as described herein above. In another preferred embodiment, a magnetic particle present in said dispersion or group of particles within the shell structure is a coated iron oxide particle, more preferably a polymer coated iron oxide particle, a latex coated iron oxide particle or a mixture thereof.

The following figures are provided for illustrative purposes. It is thus understood that figures are not to be construed as limiting. The skilled person in the art will clearly be able to envisage further modifications of the principles laid out herein.

The invention claimed is:

1. A method for collecting data by using Magnetic Particle Imaging comprising the steps of:
   (a) pre-delivering magnetic particles to a colon of a subject;
   (b) generating an imaging magnetic field with a spatial distribution of the magnetic field strength such that an area of examination in the colon consists of a first sub-area of the colon with lower magnetic field strength, where the magnetization of magnetic particles which were pre-delivered to the colon is not saturated, and a second sub-area of the colon with a higher magnetic field strength, where the magnetization of said magnetic particles is saturated;
   (c) changing the spatial location of both sub-areas in the area of examination so that the magnetization of said particles changes locally; and
   (d) acquiring signals that depend on the magnetization in the area of examination influenced by this change, wherein the area of examination in the colon comprises a portion or segment of the colon and wherein steps (b) to (d) are carried out during an entire peristaltic cycle in said colon portion or segment, followed by a reassignment of the area of examination to a different portion or segment of the colon.

2. The method of claim 1, wherein the step of changing the spatial location of the sub-areas comprises the generation of a spatially and temporarily varying magnetic field.

3. The method of claim 1, wherein an additional homogenous, temporarily variable electromagnetic focus field is employed for the reassignment of the area of examination.

4. The method of claim 1, wherein said method is combined with a method of data analysis which employs a visualization algorithm, and/or a statistical analysis method determining the quality or usability of the data.

5. The method of claim 1, wherein said magnetic particles are pre-delivered to the colon via oral uptake of a food stuff or liquid.

6. The method of claim 5, wherein said oral uptake is to be started 1 to 5 days before performing steps b-d.

7. The method of claim 1, wherein the step of pre-delivering the magnetic particles comprises pre-delivering iron oxide particles which include a gastrointestinal resistant coating or a shell structure.

8. The method of claim 7, wherein the step of pre-delivering the magnetic particles comprises pre-delivering iron oxide particles which include a gastrointestinal resistant coating that is formed from a polymer.

9. The method of claim 7, wherein the step of pre-delivering the magnetic particles comprises pre-delivering iron oxide particles which include a shell structure that is comprised of a polymer or latex.

10. The method of claim 9, wherein the step of pre-delivering the magnetic particles comprises pre-delivering iron oxide particles which include a shell structure that is comprised of a dispersion of polymer coated or latex coated iron oxide particles.

11. The method of claim 7, wherein the step of pre-delivering the magnetic particles comprises pre-delivering iron oxide particles which include a shell structure that is a non-magnetic shell structure.

12. The method of claim 1 wherein the reassignment of the area of examination comprises a reassignment to an adjacent portion or segment of the colon.

13. The method of claim 1, further comprising the step of determining a time period of the entire peristaltic cycle before performing steps (b)-(d).

14. A method for colon screening via Magnetic Particle Imaging comprising the steps of pre-delivering magnetic particles to a colon of a subject and imaging the colon via Magnetic Particle Imaging wherein said colon screening comprises examination of a portion or segment of the colon during an entire peristaltic cycle in said colon portion or segment, followed by a reassignment of the area of examination to a different portion or segment of the colon.

15. The method of claim 14 wherein the reassignment of the area of examination comprises a reassignment to an adjacent portion or segment of the colon.

16. A food stuff configured for in vivo screening for cancerous diseases of the colon, colon inflammation, polyps, gastrointestinal patency or transit, or mucosa defects of the colon by Magnetic Particle Imaging comprising a magnetic particle suitable for Magnetic Particle Imaging, wherein said magnetic particle is an iron oxide particle which includes a coating, said iron oxide particle being resistant to gastrointestinal breakdown, wherein said food stuff is free of components which enhance the excretion of the magnetic particle.

* * * * *